US011399698B2

(12) United States Patent
Oki et al.

(10) Patent No.: US 11,399,698 B2
(45) Date of Patent: Aug. 2, 2022

(54) LIGHT SOURCE SYSTEM, CONTROL DEVICE, AND CONTROL METHOD

(71) Applicant: Sony Corporation, Tokyo (JP)

(72) Inventors: Tomoyuki Oki, Kanagawa (JP); Hirotaka Muramatsu, Kanagawa (JP); Zenya Nagashima, Kanagawa (JP); Masayoshi Akita, Tokyo (JP); Akio Furukawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 110 days.

(21) Appl. No.: 16/630,466

(22) PCT Filed: May 11, 2018

(86) PCT No.: PCT/JP2018/018363
§ 371 (c)(1),
(2) Date: Jan. 13, 2020

(87) PCT Pub. No.: WO2019/017051
PCT Pub. Date: Jan. 24, 2019

(65) Prior Publication Data
US 2021/0120646 A1    Apr. 22, 2021

(30) Foreign Application Priority Data

Jul. 20, 2017    (JP) .............................. JP2017-140727

(51) Int. Cl.
*A61B 1/00*    (2006.01)
*H05B 47/10*    (2020.01)
*H05B 45/22*    (2020.01)
*A61B 1/06*    (2006.01)

(52) U.S. Cl.
CPC ........ *A61B 1/00006* (2013.01); *A61B 1/0638* (2013.01); *A61B 1/0661* (2013.01); *H05B 45/22* (2020.01); *H05B 47/10* (2020.01)

(58) Field of Classification Search
CPC . A61B 1/00006; A61B 1/0638; A61B 1/0661; A61B 1/07; H05B 45/22; H05B 47/10; F21V 23/00
See application file for complete search history.

(56) References Cited

U.S. PATENT DOCUMENTS 11,039,739 B2 *    6/2021    Morimoto ............ A61B 1/0646
2011/0237885 A1 *    9/2011    Matsubara ............. A61B 1/063
600/109

FOREIGN PATENT DOCUMENTS

DE    102012213038 A1 *    1/2014    ............ G01J 3/0289
EP    2 368 488 A1    9/2011
EP    2 850 994 A1    3/2015
(Continued)

OTHER PUBLICATIONS

Extended European Search Report dated Jun. 24, 2020 in European Patent Application No. 18835973.1, 8 pages.
(Continued)

*Primary Examiner* — Renan Luque
(74) *Attorney, Agent, or Firm* — Xsensus LLP

(57) ABSTRACT

To enable calculation a wavelength shift amount more accurately.
A light source system is provided including a light source unit configured to emit a light beam, and a calculation unit configured to calculate a wavelength shift amount of the light beam on the basis of an output from a color sensor that detects the light beam.

12 Claims, 8 Drawing Sheets

(56) References Cited

FOREIGN PATENT DOCUMENTS

| | | |
|---|---|---|
| JP | 2007-250986 A | 9/2007 |
| JP | 2009-514206 A | 4/2009 |
| JP | 2011-200410 A | 10/2011 |
| JP | 2014-035386 A | 2/2014 |

OTHER PUBLICATIONS

International Search Report and Written Opinion dated Jul. 31, 2018 for PCT/JP2018/018363 filed on May 11, 2018, 9 pages including English Translation of the International Search Report.

* cited by examiner

LIGHT SOURCE SYSTEM, CONTROL DEVICE, AND CONTROL METHOD

CROSS-REFERENCE TO RELATED APPLICATIONS

The present application is based on PCT filing PCT/JP2018/018363, filed May 11, 2018, which claims priority to JP 2017-140727, filed Jul. 20, 2017, the entire contents of each are incorporated herein by reference.

TECHNICAL FIELD

The present disclosure relates to a light source system, a control device, and a control method.

BACKGROUND ART

In a case where a semiconductor light emitting element is used as a light source, the light beam amount of an emitted light beam is controlled by changing the driving current. However, regarding a semiconductor light emitting element, if the driving current changes, the wavelength of an emitted light beam changes due to self-heating of the light source (hereinafter, this change is referred to as "wavelength shift" and furthermore the change amount of the wavelength is referred to as "wavelength shift amount"). As a result, the chromaticity (color tone) of the light beam emitted from the light source changes. It is desirable to achieve a constant level of chromaticity regardless of brightness, particularly in a medical site or the like where visual color reproducibility is strongly required. In order to suppress such a change in chromaticity, various techniques have been conventionally proposed.

For example, Patent Document 1 discloses a technique of reducing a wavelength shift amount by using a red light emitting diode (LED) light emitting element made of a nitride semiconductor similarly to green and blue LED light emitting elements. Furthermore, Patent Document 2 discloses a technique of estimating a wavelength shift amount according to the temperature of an LED light emitting element.

CITATION LIST

Patent Document

Patent Document 1: Japanese Patent Application Laid-Open No. 2007-250986
Patent Document 2: Japanese Translation of PCT International Application Publication No. 2009-514206

SUMMARY OF THE INVENTION

Problems to be Solved by the Invention

However, it has been difficult to accurately calculate the wavelength shift amount by using the technique of Patent Document 1, Patent Document 2, or the like. For example, the technique of Patent Document 1 can reduce the wavelength shift amount, but cannot calculate the wavelength shift amount. Furthermore, there is a case where even if the temperature of the LED light emitting element is the same, the wavelength shift amount differs due to deterioration or the like. Therefore, there is a case where the wavelength shift amount is not accurately calculated even by using the technique of Patent Document 2.

Therefore, the present disclosure has been made in view of the above, and the present disclosure provides a new and improved light source system, control device, and control method capable of calculating the wavelength shift amount more accurately.

Solutions to Problems

According to the present disclosure, a light source system is provided including a light source unit configured to emit a light beam, and a calculation unit configured to calculate a wavelength shift amount of the light beam on the basis of an output from a color sensor that detects the light beam.

Furthermore, according to the present disclosure, a light source system is provided including a light source unit configured to emit at least two light beams having peak wavelengths different from each other, a generating unit configured to generate a multiplexed light beam by using the at least two light beams, and a control unit configured to control the mixing ratio of the at least two light beams on the basis of output values of the at least two light beams.

Furthermore, according to the present disclosure, a control method executed by a computer is provided, the control method including emitting a light beam, and calculating a wavelength shift amount of the light beam on the basis of an output from a color sensor that detects the light beam.

Furthermore, according to the present disclosure, a control device is provided including a calculation unit configured to calculate a wavelength shift amount of a light beam emitted from a light source on the basis of an output from a color sensor that detects the light beam.

Furthermore, according to the present disclosure, a control method executed by a computer is provided, the control method including calculating a wavelength shift amount of a light beam emitted from a light source on the basis of an output from a color sensor that detects the light beam.

Effects of the Invention

As described above, according to the present disclosure, it is possible to calculate the wavelength shift amount more accurately.

Note that the effects described above are not necessarily limited, and, along with or in lieu of the effects described above, any of the effects described in the present Description, or another effect that can be grasped from the present Description may be exhibited.

MODE FOR CARRYING OUT THE INVENTION

Figure 1:
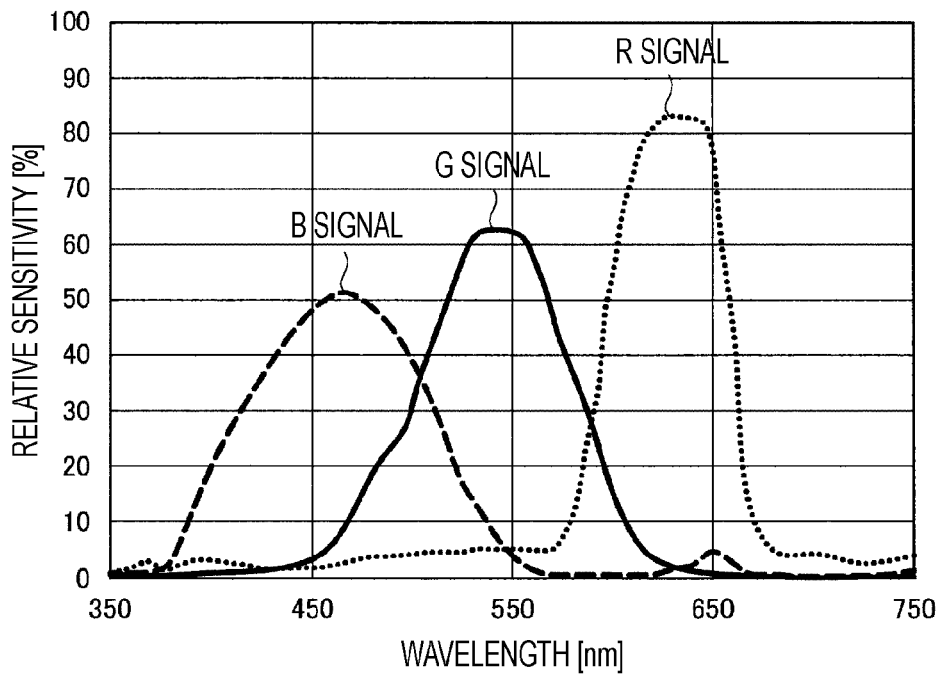
FIG. 1 is a diagram illustrating an example of spectral sensitivity characteristics of a color sensor.

Hereinafter, a preferred embodiment of the present disclosure will be described in detail with reference to the accompanying drawings. Note that in the present Description and the drawings, the same reference signs denote constituents having substantially the same functional configuration and an overlapping description will be omitted.

Note that the description will be given in the following order.
1. Background
2. Embodiment
2-1. Functional overview
2-2. Configuration
2-3. Operation
2-4. Hardware configuration
3. Conclusion

1. BACKGROUND

First, the background of the present disclosure will be described.

For example, endoscope devices are widely used as instruments for viewing the internal structure of a target. In an endoscope device, a lamp light source (for example, a xenon lamp, a halogen lamp, or the like) is often used as an illumination light source regardless of whether the endoscope device is a flexible endoscope or a rigid endoscope. In the lamp light source, since the light beam amount of an emitted light beam is controlled by a physical mechanical shutter, the chromaticity of the emitted light beam does not change even if the light beam amount of the emitted light beam is changed.

In contrast, light sources using semiconductor light emitting elements such as a laser diode (LD), an LED, or the like which is characterized by energy saving, long life, high reliability, or the like, have been actively developed. As previously described, in a case where a semiconductor light emitting element is used as a light source, the light beam amount of an emitted light beam is controlled by changing the driving current. If the driving current changes, the wavelength of an emitted light beam is shifted due to self-heating of the light source, and thus the chromaticity (color tone) of the emitted light beam from the light source changes. Such a change in wavelength due to self-heating is about several nm, and the magnitude of the wavelength shift differs for each of the colors of light beams emitted from the respective semiconductor light emitting elements.

However, especially in a medical site or the like where visual color reproducibility is strongly required, there is a possibility that the appearance of the focused-on biological part may change due to a change in wavelength of, for example, several nm, and there may also be a possibility that a doctor or the like may make a wrong judgment due to the appearance different from a conventional appearance. Therefore, it is desirable to achieve a constant level of chromaticity regardless of brightness, particularly in a medical site or the like where visual color reproducibility is strongly required. In order to suppress such a change in chromaticity, various techniques have been proposed.

For example, Patent Document 1 described above discloses a technique of reducing a wavelength shift amount by using a red LED light emitting element made of a nitride semiconductor similarly to green and blue LED light emitting elements. Furthermore, Patent Document 2 discloses a technique of estimating a wavelength shift amount according to the temperature of an LED light emitting element.

However, it has been difficult to accurately calculate the wavelength shift amount by using the technique of Patent Document 1, Patent Document 2, or the like. For example, the technique of Patent Document 1 can reduce the wavelength shift amount, but cannot calculate the wavelength shift amount. Furthermore, there is a case where even if the temperature of the LED light emitting element is the same, the wavelength shift amount differs due to deterioration or the like. Therefore, there is a case where the wavelength shift amount is not accurately calculated even by using the technique of Patent Document 2.

Furthermore, examples of the device that can directly calculate the wavelength shift amount include an optical spectrum analyzer, a spectroscopic measurement instrument, and the like; however, since such a device has a relatively larger shape than the shape of a light source, it is not appropriate that such a device is formed integrally with the light source.

In view of the circumstances described above, the disclosing party of the present case has created a technique according to the present disclosure.

Hereinafter, the present disclosure will be described in more detail.

2. EMBODIMENT

In the above description, the background of the present case has been explained. Subsequently, an embodiment according to the present disclosure will be described.

The present disclosure relates to a light source system, a control device, and a control method, and can be applied to various devices, systems, or the like. For example, the present disclosure can be applied to an endoscope device, an endoscope system, a microscope device (including a medical microscope device), a microscope system (including a medical microscope system), a projector, and the like. Note that a device and a system to which the present disclosure is applied are not particularly limited. In the present document, as an example, a case where the present disclosure is applied to an endoscope system will be described.

(2-1. Functional Overview)

First, the functional overview of the present disclosure will be described. The present disclosure calculates a wavelength shift amount of a light beam on the basis of an output from a color sensor that detects a light beam emitted from a light source. More specifically, the present disclosure calculates the wavelength shift amount on the basis of the ratio between an output having the highest value among the outputs from the color sensor (hereinafter referred to as a "main signal" and also referred to as a "first output"), and an output other than the main signal (hereinafter referred to as a "sub signal", and also referred to as a "second output").

Here, the functions of the present disclosure will be described more specifically with reference to FIGS. 1 and 2. FIG. 1 is a diagram illustrating an example of spectral sensitivity characteristics of a color sensor. As illustrated in FIG. 1, the color sensor includes a plurality of light receiving elements (for example, photodiodes, or the like) having sensitivity peaks at different wavelengths, and outputs an R signal having a sensitivity peak in the wavelength band of a red light beam, a G signal having a sensitivity peak in the wavelength band of a green light beam, and a B signal having a sensitivity peak in the wavelength band of a blue light beam.

In the example of FIG. 1, in a case where the wavelength of the green light beam shifts to the longer wavelength side, the output of the G signal that is the main signal hardly changes, whereas the output of the B signal that is the sub signal decreases. Therefore, in a case where the wavelength of a green light beam shifts to the long wavelength side, the value calculated by the following Expression 1 decreases.

[Mathematical Expression 1]

$$\frac{\text{output of } B \text{ signal}}{\text{output of } G \text{ signal}} \quad \text{[Expression 1]}$$

Here, the change amount of the value calculated by Expression 1 and the wavelength shift amount have a correlation. FIG. 2 illustrates an example of the correlation between the change amount of the value calculated by Expression 1 and the wavelength shift amount. In the example of FIG. 2, the change amount of the value calculated by Expression 1 and the wavelength shift amount have a linear (linear function) correlation relationship.

Figure 2:
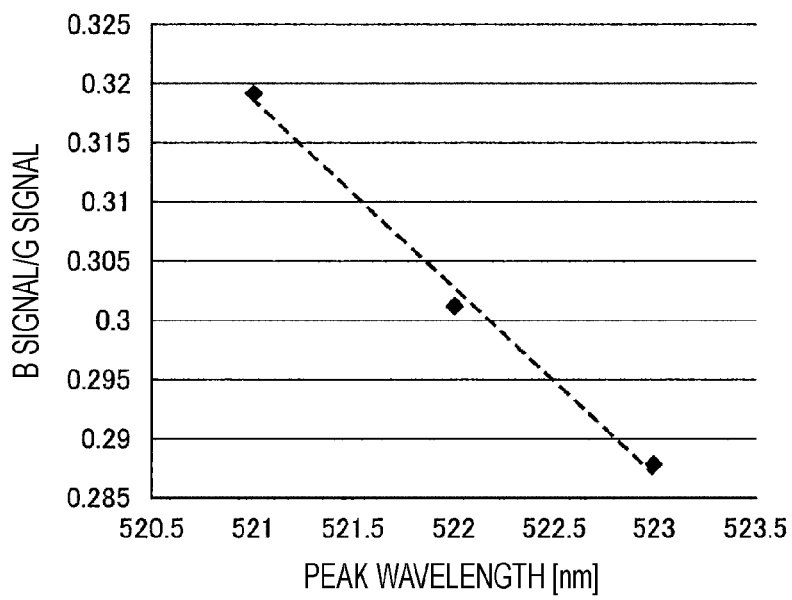
FIG. 2 is a diagram illustrating an example of a change in the ratio between a main signal and a sub signal accompanying a wavelength shift.

Then, the present disclosure calculates the wavelength shift amount of the green light beam on the basis of the correlation relationship illustrated in FIG. 2. More specifically, the present disclosure calculates the ratio between the output of the main signal and the output of the sub signal by Expression 1 upon calculation of the wavelength shift amount, obtains a peak wavelength by inputting the calculation result to the correlation illustrated in FIG. 2, and obtains a wavelength shift amount from the peak wavelength. The light source device according to the present embodiment holds information associated with the correlation relationship as illustrated in FIG. 2 for each color light beam so as to be able to obtain the wavelength shift amount of each color light beam.

With the method described above, the present disclosure can calculate the wavelength shift amount more accurately. More specifically, since the present disclosure calculates the wavelength shift amount on the basis of the actual measurement value of the color sensor, accuracy can be further improved than a technique of estimating the wavelength shift amount according to the temperature of an LED light emitting element as in, for example, Patent Document 2 described above. Furthermore, since the present disclosure can calculate the wavelength shift amount by effectively using the color sensor used for detection of a multiplexed light beam without separately providing an optical spectrum analyzer, a spectroscopic measurement instrument, or the like, the entire light source device can be downsized.

Note that the method described above is only an example, and the wavelength shift amount calculation method can be changed as appropriate. For example, in Expression 1, the output of the R signal may be used as the sub signal, and the wavelength shift amount may be calculated on the basis of the ratio between the output of the R signal and the output of the G signal. Furthermore, the ratio between the output of the main signal and the output of the sub signal may be calculated by using brute-force search, and the wavelength shift amount may be calculated on the basis of these calculation results.

Furthermore, the wavelength shift amount may be calculated not on the basis of the ratio between the output of the main signal and the output of the sub signal but only on the basis of the output of any one of the signals. However, the output of the color sensor changes not only according to the wavelength shift amount but also according to the driving current (light source output). Therefore, in the present disclosure, in the case of calculating the wavelength shift amount on the basis of any one of the signals, it is required to calculate the wavelength shift amount in consideration of also the light source output (or it is required to calculate the wavelength shift amount in a state where the light source output is made constant). In contrast, the ratio between the main signal and the sub signal does not basically change even if the light source output changes. Therefore, in the present disclosure, by calculating the wavelength shift amount on the basis of the ratio between the output of the main signal and the output of the sub signal as indicated by Expression 1, the wavelength shift amount can be calculated without considering the light source output.

Furthermore, in a case where the ratio between the output of the main signal and the output of the sub signal greatly changes along with the occurrence of wavelength shift, the present disclosure can further improve the calculation accuracy of the wavelength shift amount. For example, in a case where the value of the main signal increases and the value of the sub signal decreases along with the occurrence of the wavelength shift, the value calculated by Expression 1 changes more greatly. Therefore, the present disclosure can realize calculation of the peak wavelength and the wavelength shift amount based on the correlation relationship as illustrated in FIG. 2 with higher accuracy. Regarding the usage method of the color sensor, the main signal is mainly used in many cases; however, the present disclosure can exhibit an advantageous effect in that not only the main signal but also the sub signal is effectively used.

Furthermore, in the present disclosure, in a case where the wavelength shift amount at a certain driving current (light source output) can be calculated, the wavelength shift amount at another driving current can be obtained on the basis of this calculation result. More specifically, the driving current and the wavelength shift amount have a correlation. Therefore, in the present disclosure, by inputting the calculation result of the wavelength shift amount at a certain driving current to the correlation, the wavelength shift amount at another driving current can be obtained. As a result, the present disclosure can omit the process of calculating the wavelength shift amount for each driving current.

Then, the present disclosure can control each light source unit appropriately in consideration of the wavelength shift amount of each color light beam. For example, the present disclosure can adjust the driving condition (for example, the mixing ratio of respective color light beams or the like) of each light source unit according to the wavelength shift amount of each color light beam. As a result, the present disclosure can maintain the chromaticity (color tone) of the illumination light beam at an appropriate value at a low output where the wavelength shift does not occur and at a high output where the wavelength shift occurs.

Furthermore, the present disclosure can control each light source unit appropriately in consideration of aging deterioration. For example, the present disclosure can calculate the wavelength shift amount of each color light beam due to aging deterioration and update the driving condition of each light source unit according to the calculated wavelength shift amount.

(2-2. Configuration)

The functional overview of the present disclosure has been described above. Subsequently, the configuration of an endoscope system according to the present embodiment will be described.

Figure 3:
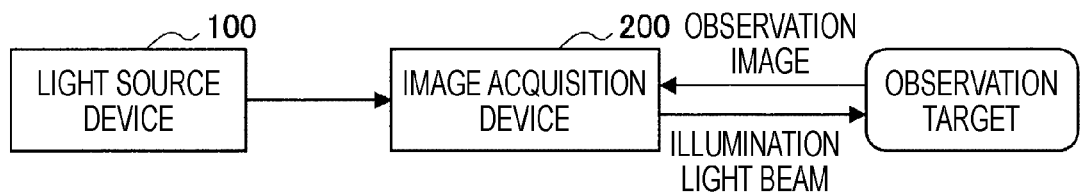
FIG. 3 is a block diagram illustrating an example of the configuration of an endoscope system.

As illustrated in FIG. 3, the endoscope system according to the present embodiment includes a light source device 100 and an image acquisition device 200. The image acquisition device 200 acquires an observation image by irradiating an observation target with an illumination light beam provided from the light source device 100.

(Light Source Device 100)

Figure 4:
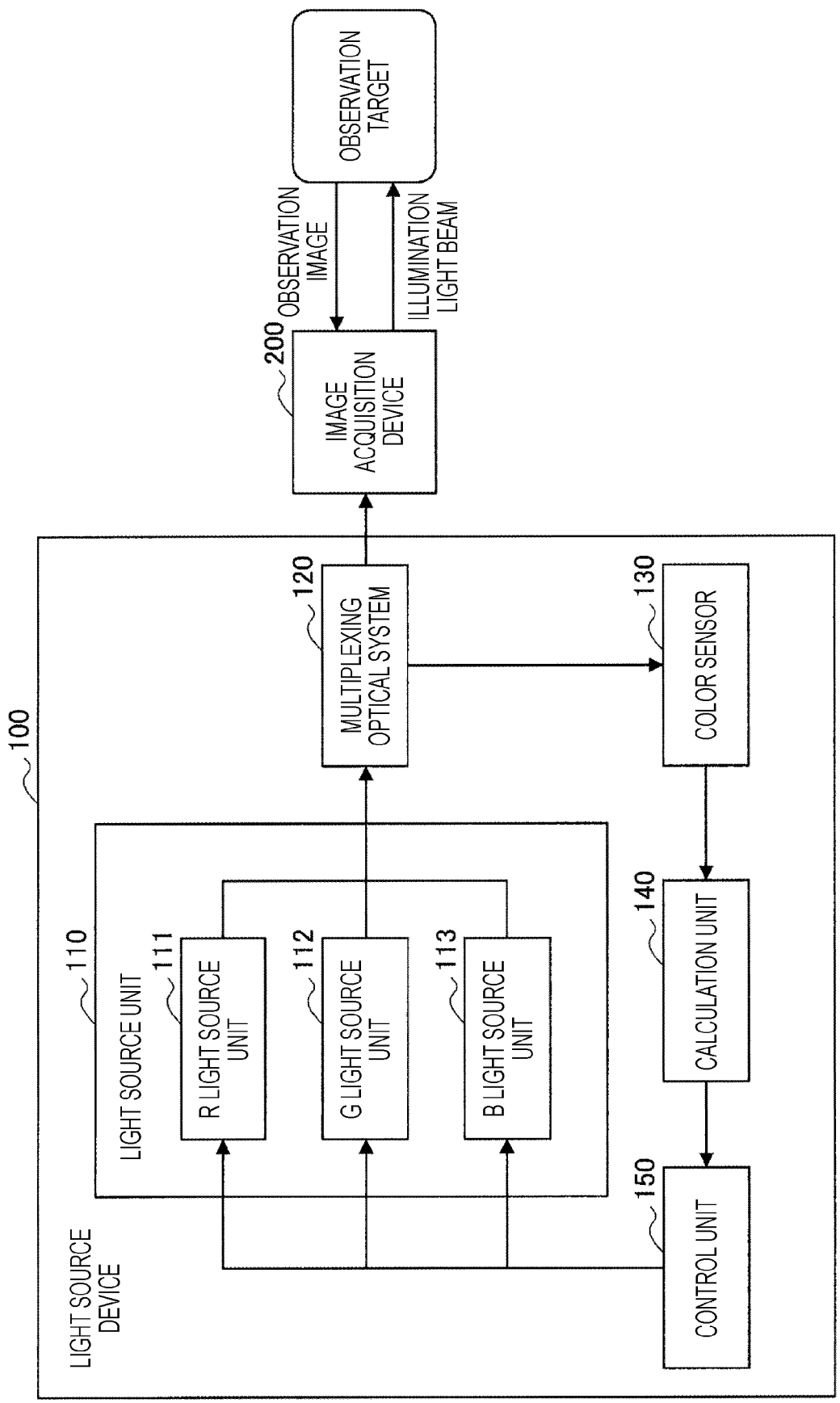
FIG. 4 is a block diagram illustrating an example of the configuration of a light source device.

First, the configuration of the light source device 100 will be described with reference to FIG. 4. As illustrated in FIG. 4, the light source device 100 includes a light source unit 110, a multiplexing optical system 120, a color sensor 130, a calculation unit 140, and a control unit 150.

The light source unit 110 includes an R light source unit 111, a G light source unit 112, and a B light source unit 113. The R light source unit 111, the G light source unit 112, and the B light source unit 113 are light sources which each emit a light beam in a predetermined wavelength band. More specifically, each of the R light source unit 111, the G light source unit 112, and the B light source unit 113 is configured to emit a light beam having a peak intensity in a specific band, the R light source unit 111 emits a red light beam, the G light source unit 112 emits a green light beam, and the B light source unit 113 emits a blue light beam. Note that the light beams emitted from the light source unit 110 are not limited to the light beams described above. For example, the light source unit 110 may emit a white light beam or the like separately in addition to the light beams described above.

As the light source unit 110, for example, a semiconductor laser light source can be used. By using various semiconductor laser light sources, it is possible to further downsize the light source device. Such a semiconductor laser light source is not particularly limited; however, in the present document, a description will be given assuming that, as an example, a GaInP quantum well structure laser diode using a GaInP semiconductor is used as the R light source unit 111, and a GaInN quantum well structure laser diode using a GaInN semiconductor is used as each of the G light source unit 112 and the B light source unit 113.

Note that a light source other than the semiconductor laser light source may be used as the light source unit 110. For example, an LED light source may be used as the light source unit 110. In a case where an LED light source is used, there is a case where not a wavelength shift to the long wavelength side but a wavelength shift to the short wavelength side may occur (for example, a light source made of GaN-based material, or the like). Even in this case, the wavelength shift amount can be calculated by the method similar to the method described above. That is, the shift direction of the wavelength shift is not particularly limited.

The multiplexing optical system 120 functions as a generating unit that multiplexes the respective color light beams emitted from the light source unit 110 to generate a white light beam used as an illumination light beam. Note that any configuration and any multiplexing method of the multiplexing optical system 120 may be adopted. Here, an example of the configuration of the multiplexing optical system 120 according to the present embodiment will be described with reference to FIG. 5.

Figure 5:
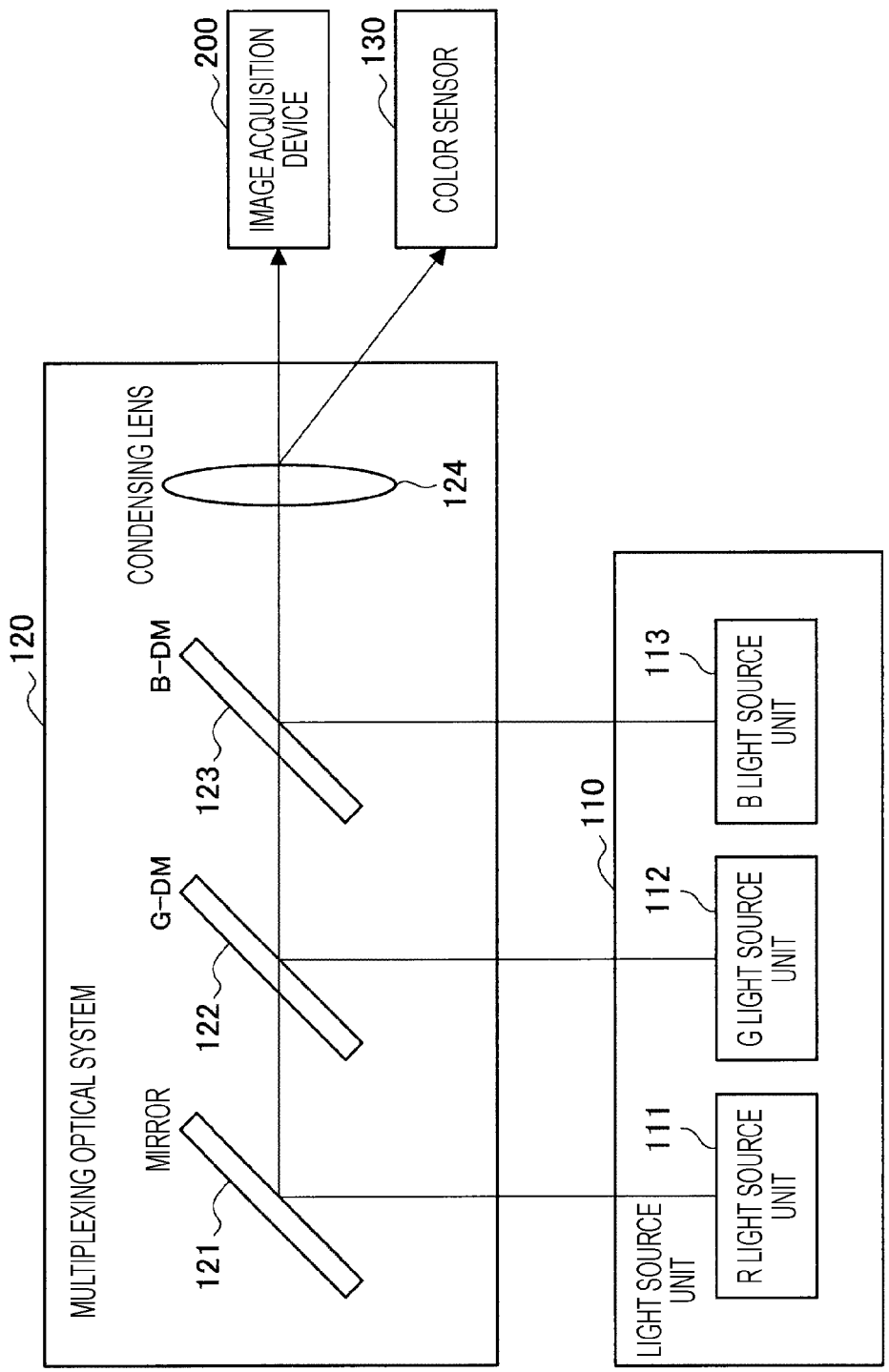
FIG. 5 is a block diagram illustrating an example of the configuration of a multiplexing optical system.

As illustrated in FIG. 5, the multiplexing optical system 120 according to the present embodiment includes, for example, a mirror 121, two types of dichroic mirrors (denoted by "G-DM122" and "B-DM123" in FIG. 5), and a condensing lens 124.

The optical path of the red light beam emitted from the R light source unit 111 is switched by the mirror 121, and the red light beam is transmitted through the two types of dichroic mirrors (G-DM122 and B-DM123) and enters the condensing lens 124. The optical path of the green light beam emitted from the G light source unit 112 is switched by the G-DM122 having characteristics of transmitting a light beam having a wavelength longer than that of the red light beam and reflecting the green light beam, and thus the green light beam is multiplexed with the red light beam, is transmitted through the B-DM123, and enters the condensing lens 124. The optical path of the blue light beam emitted from the B light source unit 113 is switched by the B-DM123 having characteristics of transmitting a light beam having a wavelength longer than that of the green light beam and reflecting the blue light beam, and thus the blue light beam is multiplexed with the red light beam and the green light beam and enters the condensing lens 124.

The multiplexed light beam collected by the condensing lens 124 enters the image acquisition device 200. Note that the configuration illustrated in FIG. 5 is only an example, and can be changed as appropriate. For example, a collimating lens or the like that generates parallel light beams by transmitting light beams may be provided as appropriate, or a rod integrator or the like that equalizes in-plane intensity of each color light beam may be provided on a subsequent stage of the condensing lens 124.

The color sensor 130 is an RGB color sensor that can detect an emitted light beam by dividing the emitted light beam into an R signal, a G signal, and a B signal; however, is not limited to this. For example, the color sensor 130 may be any sensor as long as the color sensor can output a main signal and a sub signal with respect to an emitted light beam.

Upon calculation of the wavelength shift amount, the color sensor 130 receives each color light beam individually. Here, as long as the color sensor 130 can receive each color light beam individually, the location where the color sensor 130 is provided is not particularly limited. For example, the color sensor 130 may be provided on the subsequent stage of the multiplexing optical system 120. As a result, the light source unit 110 emits each color light beam individually, and thus only one color sensor 130 can receive each color light beam individually. Of course, the color sensor 130 may be provided on the subsequent stage of each of the light source units of the respective color beams (R light source unit 111, G light source unit 112, B light source unit 113).

Note that the color sensor 130 may receive any light beam as long as the light beam is part of the emitted light beam. For example, the color sensor 130 may receive any of a direct light beam, a scattered light beam, a reflected light beam, or a stray light beam emitted from the multiplexing optical system 120. The color sensor 130 provides the R signal, the G signal, and the B signal to the calculation unit 140 as outputs.

The calculation unit 140 calculates the wavelength shift amount of each color light beam on the basis of outputs from the color sensor 130. More specifically, upon calculation of the wavelength shift amount of each color light beam, the calculation unit 140 calculates the ratio between the main signal and the sub signal as indicated in Expression 1, inputs the calculation result to the correlation illustrated in FIG. 2, and thus calculates the wavelength shift amount. Note that as described above, the method for calculating the wavelength shift amount is not particularly limited. The calculation unit 140 provides information associated with the calculated wavelength shift amount to the control unit 150.

Note that the timing at which the calculation unit 140 calculates the wavelength shift amount is any timing. For example, the calculation unit 140 may calculate the wavelength shift amount at a specific timing (for example, a timing when the light source device 100 is activated, or the like), or may calculate the wavelength shift amount at a predetermined interval (for example, a several hours interval, or the like). Furthermore, the calculation unit 140 may calculate the wavelength shift amount in a case where the occurrence of wavelength shift is detected by a predetermined method (for example, in a case where the occurrence of wavelength shift is detected by an image analysis, or the like), or may calculate the wavelength shift amount on the basis of a user instruction (for example, in a case where a user notices the wavelength shift, or the like).

The control unit 150 realizes light source control considering the wavelength shift amount. More specifically, first, the control unit 150 determines the light beam amount of entirety of the illumination light beam. The method for determining the light beam amount of the illumination light beam is any method. For example, the control unit 150 may determine the light beam amount of an illumination light beam on the basis of the separation distance between an emission port and an observation target, or may determine the light beam amount of an illumination light beam on the basis of a user instruction.

Then, the control unit 150 sets a combination (mixing ratio) of respective color beams that is optimal for the light beam amount of the illumination light beam on the basis of driving condition information. The driving condition information that is referred to upon setting of the mixing ratio includes information in which the light beam amount of the illumination light beam is associated with the mixing ratio of the respective color light beams emitted from the respective light source units. In this driving condition information, the mixing ratio of the respective color light beams is set so that the chromaticity (color tone) of the illumination light beam is constant for each light beam amount of the illumination light beam.

Then, the control unit 150 calculates the light beam amount of each color light beam on the basis of the mixing ratio of the respective color light beams, and calculates the driving current for emitting the light beam of the calculated light beam amount. The driving condition information also includes information associated with the driving current for emitting a light beam of each light beam amount for each light source unit, and the control unit 150 calculates the driving current of each light source unit for realizing the light beam amount of each color light beam.

At this time, the control unit 150 can adjust (calibrate) the driving condition information on the basis of the wavelength shift amount calculated by the calculation unit 140. More specifically, the control unit 150 can adjust the information associated with the optimum mixing ratio of the respective color beams and the driving current for emitting a light beam of each light beam amount on the basis of the wavelength shift amount. Therefore, in a case where a wavelength shift occurs, it is possible for the control unit 150 to maintain the chromaticity (color tone) of the illumination light beam at an appropriate value. Note that the control unit 150 may only temporarily adjust the driving condition information, and may update (rewrite) the driving condition information, for example, in a case where a wavelength shift occurs due to aging deterioration, or the like.

Note that the processing content of the control unit 150 is not limited to the processing content described above. For example, the control unit 150 may notify a user of the occurrence of wavelength shift by controlling an output unit (not illustrated, including a display unit such as a display, a sounding unit such as a speaker, and the like) in a case where a wavelength shift (including a wavelength shift due to aging deterioration) occurs.

(Image Acquisition Device 200)

Figure 6:
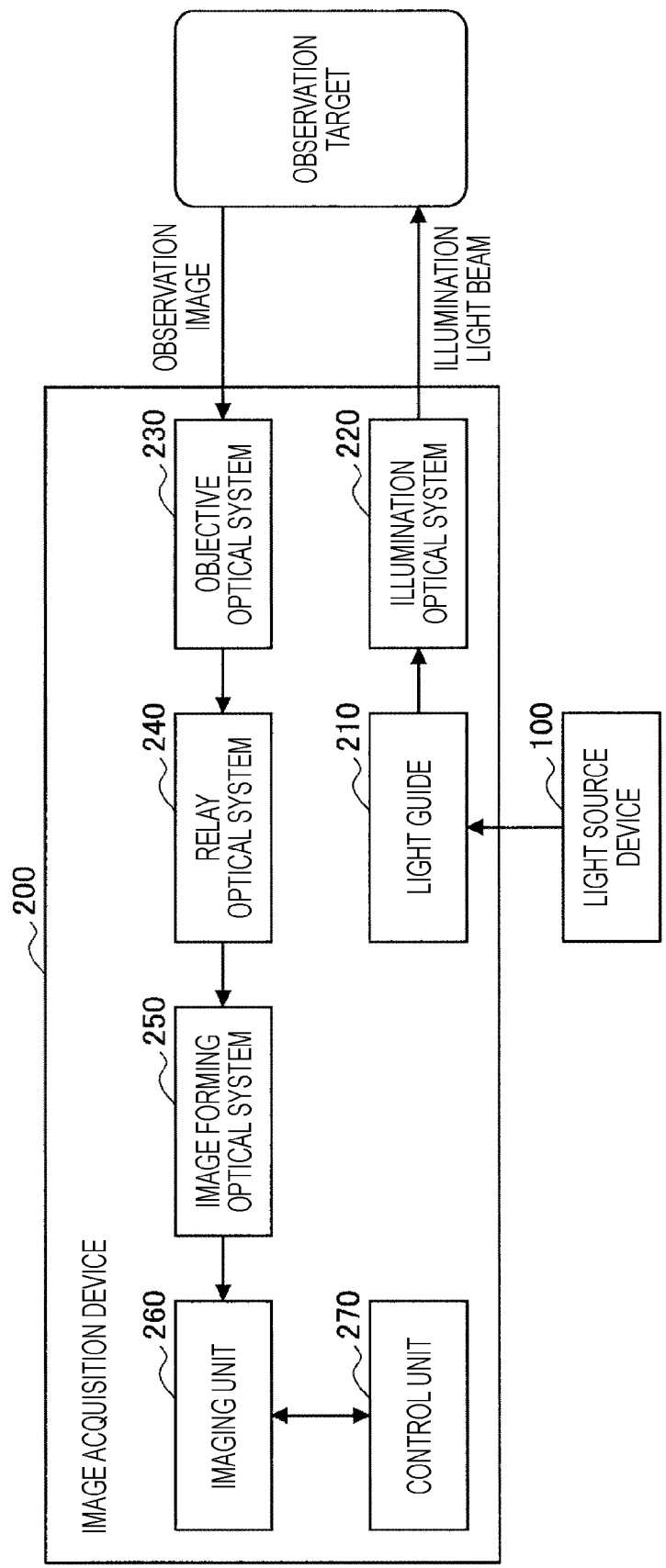
FIG. 6 is a block diagram illustrating an example of the configuration of an image acquisition device.

Subsequently, the configuration of the image acquisition device 200 will be described with reference to FIG. 6. As illustrated in FIG. 6, the image acquisition device 200 includes a light guide 210, an illumination optical system 220, an objective optical system 230, a relay optical system 240, an image forming optical system 250, an imaging unit 260, and a control unit 270.

The light guide 210 is usually an index guide type in which a plurality of multimode optical fibers having a core diameter of about 10 [µm] to 80 [µm] is bound (bundled). The light guide 210 is connected to the light source device 100 and guides the multiplexed light beam input by the light source device 100 to the illumination optical system 220. Such a light guide 210 is not particularly limited, and it is possible to use various known light guides can be used.

The illumination optical system 220 is an optical system that adjusts the image formation state of the illumination light beam propagated by the light guide 210 onto an observation target. Such an illumination optical system 220 is not particularly limited, and it is possible to use various known illumination optical systems.

The objective optical system 230 is an optical system for obtaining an observation image of a region irradiated with the illumination light beam. Such an objective optical system 230 is not particularly limited, and various known optical systems can be used. The observation image propagated by the objective optical system 230 is further guided to the image forming optical system 250 by the relay optical system 240.

The relay optical system 240 is an optical system that relays an image observed by the objective optical system 230 to the image forming optical system 250. Note that the relay optical system 240 is not particularly limited, and it is possible to use various known relay optical systems.

The image forming optical system 250 is an optical system for forming an observation image of the observation target propagated by the relay optical system 240 on the imaging unit 260, and is optically connected to the imaging unit 260 on the subsequent stage. Such an image forming optical system 250 is not particularly limited, and it is possible to use various known image forming optical systems.

The imaging unit 260 is configured to generate image data of a captured image by capturing an observation image inside a living body formed by an illumination light beam from the light source device 100 under control of the control unit 270. More specifically, the imaging unit 260 uses an imaging element (for example, a charge coupled device (CCD), a complementary metal oxide semiconductor (CMOS), or the like) having sensitivity in the wavelengths in a visible light band to capture an image in a situation close to a situation directly observed with human eyes, to appropriately develop such an image, and to provide such an image to a display unit (not illustrated, a display or the like)

as an observation image. Thus, the imaging unit 260 enables an observer to confirm the observation image through the display unit.

The control unit 270 is configured to control the overall functions of the image acquisition device 200 and is a unit corresponding to a camera control unit (CCU) of the endoscope system. For example, the control unit 270 controls the imaging unit 260 to realize the imaging process of the observation target.

Furthermore, the control unit 270 may control the light source device 100. For example, the control unit 270 may generate a control signal on the basis of the imaging result, may provide the generated control signal to the light source device 100, and may adjust the illumination light beam. Furthermore, the control unit 270 may detect the occurrence of a wavelength shift by analyzing the captured image, and may instruct the light source device 100 to calculate the wavelength shift amount and to control the light source considering the wavelength shift amount.

(2-3. Operation)

The configuration of the endoscope system according to the present embodiment has been described above. Subsequently, the operation of the endoscope system according to the present embodiment will be described.

(Calculation of Wavelength Shift Amount)

Figure 7:
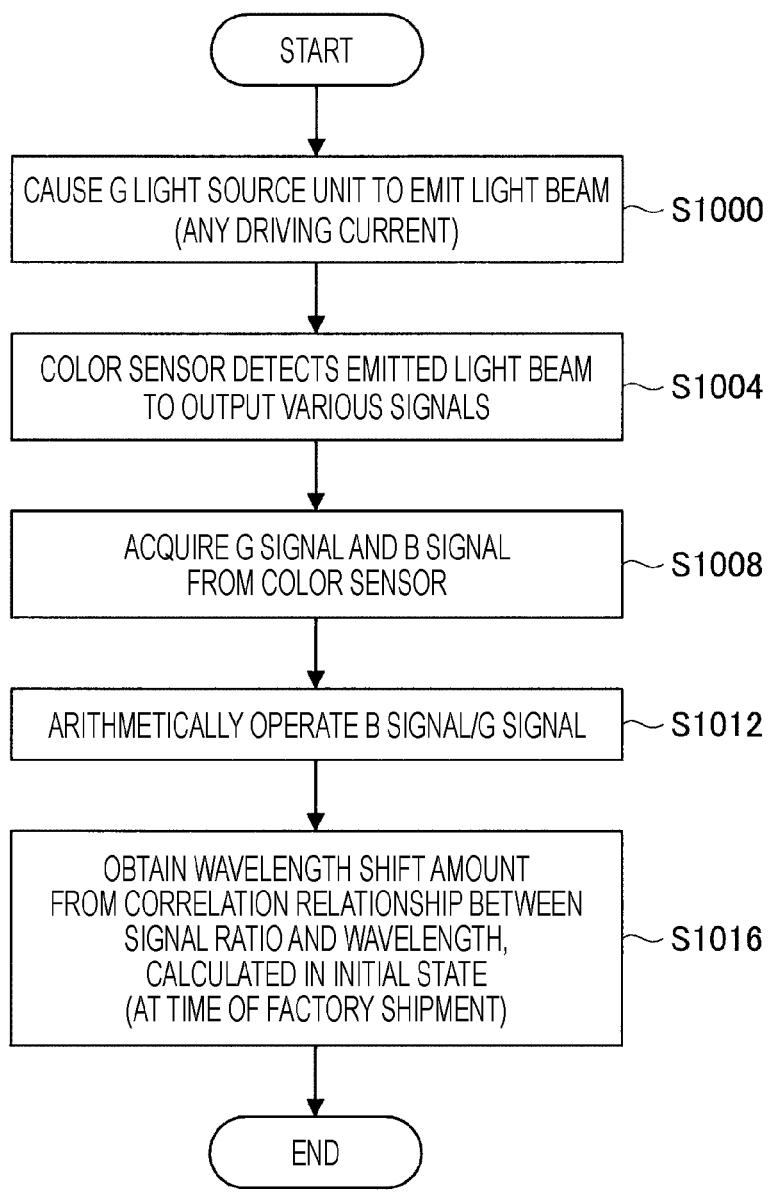
FIG. 7 is a flowchart illustrating an example of the wavelength shift amount calculating operation.

First, the calculation operation of the wavelength shift amount of each color light beam will be described with reference to FIG. 7. FIG. 7 illustrates, as an example, an operation for calculating the wavelength shift amount of the green light beam.

In step S1000, the control unit 150 controls the G light source unit 112 to emit a light beam so as to cause the G light source unit 112 to emit a green light beam. Note that the magnitude of the driving current at this time is any. In step S1004, the color sensor 130 detects the emitted light beam and outputs various signals (R signal, G signal, and B signal). In step S1008, the calculation unit 140 acquires the G signal that is the main signal and the B signal that is the sub signal output by the color sensor 130. In step S1012, the calculation unit 140 obtains the ratio between the main signal and the sub signal (the value obtained by dividing the value of the sub signal by the value of the main signal). In step S1016, the calculation unit 140 obtains the wavelength shift amount on the basis of the correlation relationship between the ratio between the main signal and the sub signal and the wavelength calculated in the initial state (for example, at the time of factory shipment). Note that the operation described above is also performed for the red light beam and the blue light beam other than the green light beam.

This operation enables the calculation unit 140 to calculate the wavelength shift amount of each color light beam more accurately.

(Light Source Control Operation Considering Wavelength Shift Amount)

Figure 8:
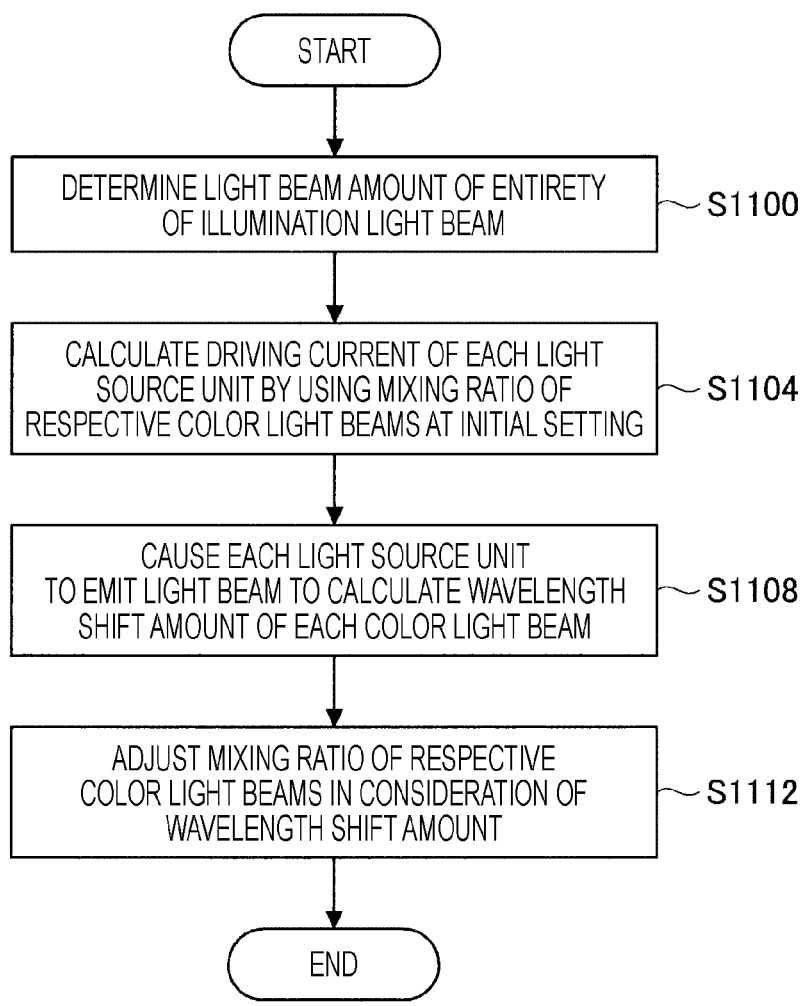
FIG. 8 is a flowchart illustrating an example of a light source control operation considering the wavelength shift amount.

Subsequently, with reference to FIG. 8, a light source control operation considering the wavelength shift amount will be described.

In step S1100, the control unit 150 determines the light beam amount of entirety of the illumination light beam. In step S1104, the control unit 150 calculates the driving current of each light source unit by using the mixing ratio of the respective color light beams at the initial setting (for example, at the time of factory shipment). More specifically, the control unit 150 obtains the light beam amount of each color light beam on the basis of the mixing ratio of the respective color light beams, and calculates the driving current of each light source unit.

In step S1108, the control unit 150 causes each light source unit to emit a light beam individually, and the calculation unit 140 calculates the wavelength shift amount of each color light beam by the operation of FIG. 7. Note that in lieu of calculating the wavelength shift amount in step S1108, the control unit 150 obtains the wavelength shift amount in the driving current calculated in step S1104, on the basis of the previously calculated wavelength shift amount in a certain driving current. In step S1112, the control unit 150 adjusts the mixing ratio of the respective color light beams in consideration of the wavelength shift amount.

With the operation described above, the control unit 150 can emit an appropriate illumination light beam in consideration of the wavelength shift amount. In other words, the control unit 150 can maintain the chromaticity (color tone) of the illumination light beam at an appropriate value even in a case where wavelength shift occurs.

(Light Source Control Operation Considering Aging Deterioration)

Figure 9:
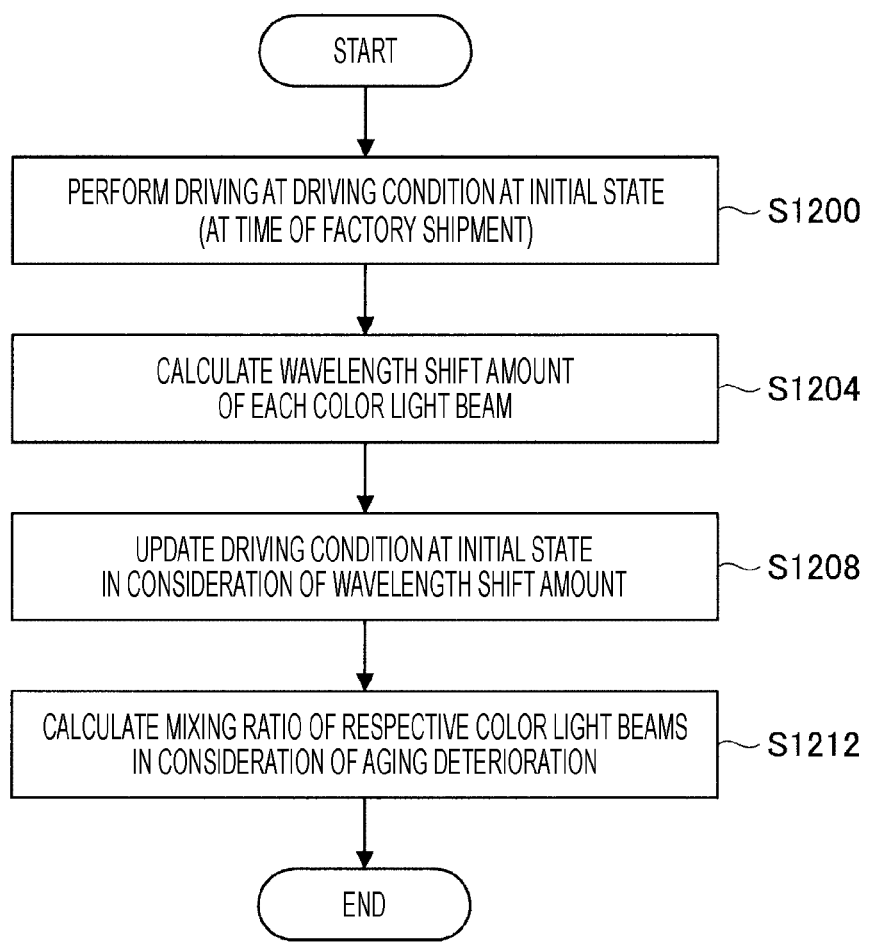
FIG. 9 is a flowchart illustrating an example of the light source control operation considering aging deterioration.

Subsequently, with reference to FIG. 9, a light source control operation considering aging deterioration will be described.

In step S1200, the control unit 150 drives each light source unit on the basis of the driving condition information in an initial state (for example, at the time of factory shipment). In step S1204, the calculation unit 140 calculates the wavelength shift amount of each color light beam by the operation of FIG. 7. In step S1208, the control unit 150 updates (rewrites) the driving condition information in the initial state in consideration of the wavelength shift amount of each color light beam. In step S1212, the control unit 150 calculates the mixing ratio of the respective color light beams considering aging deterioration on the basis of the updated driving condition information.

With the operation described above, the control unit 150 can appropriately perform light source control in consideration of aging deterioration. Note that the operation described above does not need to be performed every time the light source device is used, and it is assumed that the operation described above is performed at a timing at which aging deterioration may occur according to the characteristics of each light source unit.

(2-4. Hardware Configuration)

Next, the hardware configuration of the control unit 150 of the light source device 100 will be described in detail with reference to FIG. 10.

Figure 10:
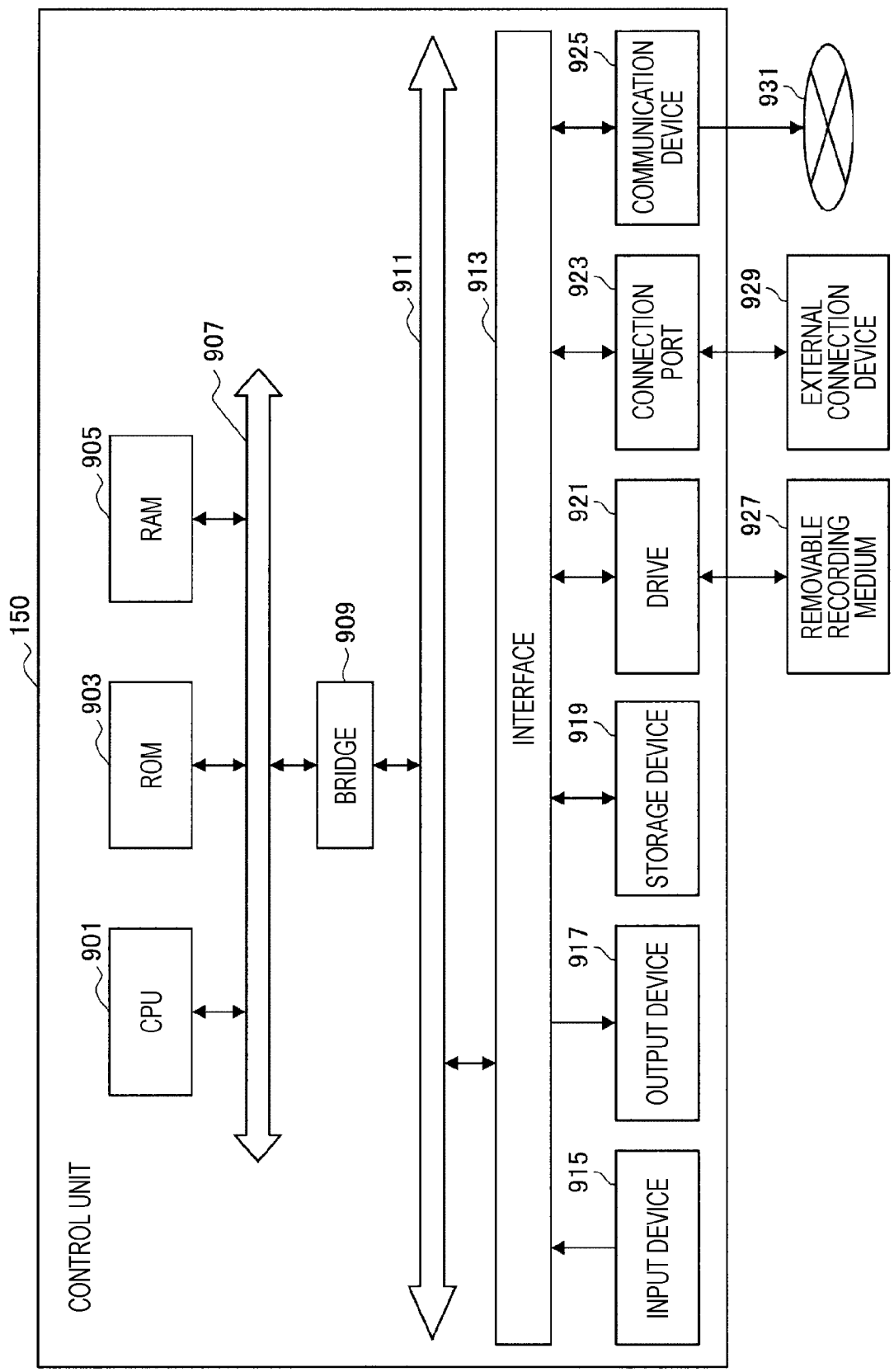
FIG. 10 is a block diagram illustrating an example of the hardware configuration of a control unit.

As illustrated in FIG. 10, the control unit 150 mainly includes a CPU 901, a ROM 903, and a RAM 905. Furthermore, the control unit 150 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls the entire or part of the operation in the control unit 150 or the light source device 100 in accordance with various programs recorded in the ROM 903, the RAM 905, the storage device 919, or a removable recording medium 927. The ROM 903 stores programs, arithmetic parameters, and the like that the CPU 901 uses. The RAM 905 primarily stores programs that the CPU 901 uses, parameters that appropriately change in execution of the programs, and the like. The CPU 901, the ROM 903, and the RAM 905 are connected to one another by a host bus 907 configured of an internal bus such as a CPU bus.

The host bus 907 is connected to the external bus 911 such as a peripheral component interconnect/interface (PCI) bus via the bridge 909.

The input device 915 is an operation means such as a mouse, a keyboard, a touch panel, a button, a switch, a lever, or the like, operated by the user. Furthermore, the input device 915 may be, for example, a remote control means (so-called a remote controller) using infrared rays or other radio waves, or an external connection device 929 such as a mobile phone, a PDA, or the like corresponding to operation of the control unit 150. Moreover, the input device 915 is configured of, for example, an input control circuit or the like that generates an input signal on the basis of information input by the user by using the operation means described above and outputs the input signal to the CPU 901. By operating the input device 915, the user can input various pieces of data to the control unit 150 and instruct the control unit 150 to perform processing operation.

The output device 917 is configured of a device capable of visually or aurally notifying the user of the acquired information. Examples of such a device include a display device such as a CRT display device, a liquid crystal display device, a plasma display device, an EL display device, a lamp or the like, an audio output device such as a speaker or a headphone, a printer device, a mobile phone, a facsimile, and the like. The output device 917 outputs, for example, results obtained by various processes performed by the control unit 150. Specifically, the display device displays the results obtained by various processes performed by the control unit 150 as text or images. On the other hand, the audio output device converts an audio signal made of reproduced audio data, acoustic data, or the like into an analog signal and outputs the analog signal.

The storage device 919 is a data storage device configured as an example of a memory unit of the control unit 150. The storage device 919 is configured of, for example, a magnetic memory unit device such as a hard disk drive (HDD), a semiconductor memory device, an optical memory device, a magneto-optical memory device, or the like. The storage device 919 stores programs executed by the CPU 901, various pieces of data, various pieces of data acquired from the outside, and the like.

The drive 921 is a reader/writer for a recording medium, and is built in or externally fitted to the control unit 150. The drive 921 reads information recorded in an attached removable recording medium 927 such as a magnetic disk, an optical disk, a magneto-optical disk, a semiconductor memory, or the like, and outputs the information to the RAM 905. Furthermore, the drive 921 can write a record on the attached removable recording medium 927 such as a magnetic disk, an optical disk, a magneto-optical disk, a semiconductor memory, or the like.

Examples of the removable recording medium 927 include, for example, a DVD medium, an HD-DVD medium, a Blu-ray (registered trademark) medium, and the like. Furthermore, the removable recording medium 927 may be a Compact Flash (CF) (registered trademark), a flash memory, a secure digital memory card (SD memory card), or the like. Furthermore, the removable recording medium 927 may be, for example, an integrated circuit card) (IC card), an electronic device, or the like equipped with a non-contact IC chip.

The connection port 923 is a port for directly connecting a device to the control unit 150. Examples of the connection port 923 include a universal serial bus (USB) port, an IEEE1394 port, a small computer system interface (SCSI) port, and the like. Other examples of the connection port 923 include an RS-232C port, an optical audio terminal, a high-definition multimedia interface (HDMI) (registered trademark) port, and the like. By connecting the external connection device 929 to the connection port 923, the control unit 150 acquires various pieces of data directly from the external connection device 929 or provides various pieces of data to the external connection device 929.

The communication device 925 is a communication interface configured of a communication device or the like for connecting to a communication network 931, for example. The communication device 925 is, for example, a communication card or the like for wired or wireless local area network (LAN), Bluetooth (registered trademark), or a wireless USB (WUSB). Furthermore, the communication device 925 may be a router for optical communication, a router for asymmetric digital subscriber line (ADSL), a modem for various types of communication, or the like. The communication device 925 can transmit and receive a signal or the like according to a predetermined protocol such as TCP/IP or the like to and from, for example, the Internet or another communication device. Furthermore, the communication network 931 connected to the communication device 925 is configured of a network or the like connected by wire or wireless, and may be, for example, the Internet, a Home LAN, infrared communication, radio wave communication, satellite communication, or the like.

An example of the hardware configuration capable of realizing the functions of the control unit 150 according to the present embodiment has been described above. Each of the constituents described above may be configured using a general-purpose member, or may be configured of hardware specialized for the function of each constituent. Therefore, the hardware configuration to be used can be changed as appropriate according to the technical level at each time of implementing the embodiment described above.

3. CONCLUSION

As described above, according to the present disclosure, the wavelength shift amount of an emitted light beam can be calculated on the basis of an output from the color sensor 130 that detects a light beam emitted from the light source. For example, the present disclosure can calculate the wavelength shift amount on the basis of the ratio between the main signal and the sub signal. As a result, the present disclosure can calculate the wavelength shift amount more accurately. More specifically, since the present disclosure calculates the wavelength shift amount according to the actual measurement value of the color sensor, accuracy can be further improved than a technique of estimating the wavelength shift amount according to the LED light emitting element as in, for example, Patent Document 2 described above.

Furthermore, since the present disclosure can calculate the wavelength shift amount by effectively using the color sensor 130 used for detection of a multiplexed light beam without separately providing an optical spectrum analyzer, a spectroscopic measurement instrument, or the like, the entire light source device 100 can be downsized.

Furthermore, the present disclosure can realize light source control in consideration of the wavelength shift amount. For example, the present disclosure can adjust the mixing ratio of the respective color light beams in consideration of the wavelength shift amount. As a result, the present disclosure can maintain the chromaticity (color tone) of the illumination light beam at an appropriate value at a low output where the wavelength shift does not occur and at a high output where the wavelength shift occurs. Furthermore, the present disclosure can realize light source control considering aging deterioration. For example, the present disclosure can update the driving conditions in the initial settings on the basis of the wavelength shift amount due to aging deterioration.

While the preferred embodiment of the present disclosure has been described in detail with reference to the accompanying drawings, the technical scope of the present disclosure is not limited to such an example. It is obvious that a person skilled in the art to which the present disclosure pertains can conceive various modifications and corrections within the scope of the technical idea described in the claims, and it is naturally understood that these also belong to the technical scope of the present disclosure.

For example, the various processes described above may be realized by machine learning (or artificial intelligence (AI) or the like). For example, the wavelength shift amount may be obtained by learning the correlation relationship between output of the color sensor 130 and the wavelength shift amount in advance so that the calculation unit 140 of the light source device 100 inputs an output from the color sensor 130 into the result of the learning. Similarly, on the basis of the result of machine learning, the control unit 150 of the light source device 100 may perform light source control considering the wavelength shift amount (for example, adjustment, update, or the like of driving condition information), or the control unit 270 of the image acquisition device 200 may analyze a captured image and detect a wavelength shift.

Furthermore, the respective steps illustrated in the flowcharts described above do not necessarily have to be processed in time series in the order described in the flowchart. That is, the respective steps may be processed in an order different from the order described in the flowchart, or may be processed in parallel.

Furthermore, the functional configuration of the light source device 100 or the image acquisition device 200 may be changed as appropriate. More specifically, some of the functions of the light source device 100 or the image acquisition device 200 may be realized by an external device as appropriate. For example, the functions of the control unit 150 of the light source device 100 may be realized by the control unit 270 of the image acquisition device 200. In contrast, the functions of the control unit 270 of the image acquisition device 200 may be realized by the control unit 150 of the light source device 100. Furthermore, some of the functions of the light source device 100 may be realized by the control unit 150. For example, the function of the calculation unit 140 of the light source device 100 may be realized by the control unit 150. Furthermore, some of the functions of the image acquisition device 200 may be realized by the control unit 270. For example, some of the functions of the imaging unit 260 may be realized by the control unit 270.

Furthermore, the effects described in the present Description are illustrative or exemplary only and are not restrictive. That is, the technique according to the present disclosure can exhibit other effects that are apparent to those skilled in the art from the description of the present Description in addition to or in lieu of the effects described above.

Note that the following configurations also belong to the technical scope of the present disclosure.

(1)

A light source system including:

a light source unit configured to emit a light beam; and a calculation unit configured to perform calculation of a wavelength shift amount of the light beam on the basis of an output from a color sensor that detects the light beam.

(2)

The light source system according to the (1), in which the calculation unit performs the calculation on the basis of a first output having a highest value among a plurality of outputs from the color sensor.

(3)

The light source system according to the (2), in which the calculation unit performs the calculation also on the basis of a second output which is an output other than the first output among the plurality of outputs from the color sensor.

(4)

The light source system according to the (3), in which the calculation unit performs the calculation on the basis of a ratio between the first output and the second output.

(5)

The light source system according to the (4), in which the calculation unit performs the calculation on the basis of correlation between a change amount of the ratio and the wavelength shift amount.

(6)

The light source system according to any one of the (1) to the (5), in which the light source unit emits at least two light beams having peak wavelengths different from each other, and the light source system further includes a generating unit configured to generate a multiplexed light beam by using the at least two light beams.

(7)

The light source system according to the (6), further including a control unit configured to control outputs of the at least two light beams on the basis of the wavelength shift amount.

(8)

The light source system according to the (7), in which the control unit controls a mixing ratio of the at least two light beams.

(9)

The light source system according to any one of the (6) to the (8), in which the color sensor is provided on a subsequent stage of the generating unit.

(10)

The light source system according to any one of the (1) to the (9), in which the color sensor detects at least one of a direct light beam, a scattered light beam, a reflected light beam, or a stray light beam.

(11)

The light source system according to any one of the (1) to the (10), in which the light source unit emits a light beam by using a semiconductor light emitting element.

(12)

The light source system according to the (6), in which the generating units generates a white beam as the multiplexed light beam, and the light source system further includes an imaging unit configured to capture an image of an object to be irradiated with the white light beam.

(13)

The light source system according to the (12), in which the light source system is an endoscope system or a microscope system.

(14)

A light source system including:

a light source unit configured to emit at least two light beams having different peak wavelengths;

a generating unit configured to generate a multiplexed light beam by using the at least two light beams; and a control unit configured to control a mixing ratio of the at least two light beams on the basis of output values of the at least two light beams.

(15)

A control method executed by a computer, the control method including:

emitting a light beam; and calculating a wavelength shift amount of the light beam on the basis of an output from a color sensor that detects the light beam.

(16)

A control device including a calculation unit configured to calculate a wavelength shift amount of a light beam emitted from a light source on the basis of an output from a color sensor that detects the light beam.

(17)

A control method executed by a computer, the control method including calculating a wavelength shift amount of a light beam emitted from a light source on the basis of an output from a color sensor that detects the light beam.

REFERENCE SIGNS LIST

100 Light source device
110 Light source unit
111 R light source unit
112 G light source unit
113 B Light source unit
120 Multiplexing optical system
130 Color sensor
140 Calculation unit
150 Control unit
200 Image acquisition device
210 Light guide
220 Illumination optical system
230 Objective optical system
240 Relay optical system
250 Image forming optical system
260 Imaging unit
270 Control unit

The invention claimed is:

1. A light source system comprising:

a light source configured to emit at least two light beams having peak wavelengths different from each other and to generate a multiplexed light beam by using the at least two light beams:

a color sensor configured to detect the multiplexed light beam emitted by the light source and produce a plurality of outputs including a first output and a second output based on the multiplexed light beam; and circuitry configured to perform calculation of a wavelength shift amount of the light multiplexed beam on a basis of a ratio of the first output and the second output produced by the color sensor.

2. The light source system according to claim 1, wherein the circuitry is further configured to perform the calculation on a basis of the first output having a highest value among a plurality of outputs from the color sensor.

3. The light source system according to claim 2, wherein the second output is an output other than the first output among the plurality of outputs from the color sensor.

4. The light source system according to claim 1, wherein the circuitry is further configured to perform the calculation on a basis of correlation between a change amount of the ratio and the wavelength shift amount.

5. The light source system according to claim 1, wherein the circuitry is further configured to control outputs of the at least two light beams on a basis of the wavelength shift amount.

6. The light source system according to claim 5, wherein the circuitry is further configured to control a mixing ratio of the at least two light beams.

7. The light source system according to claim 1, wherein the color sensor detects at least one of a direct light beam, a scattered light beam, a reflected light beam, or a stray light beam.

8. The light source system according to claim 1, wherein the light source includes a semiconductor light emitter to emit the at least two light beams.

9. The light source system according to claim 1, wherein the light source generates a white light beam as the multiplexed light beam, and wherein the light source system further comprises an imager configured to capture an image of an object to be irradiated with the white light beam.

10. The light source system according to claim 9, wherein the light source system is an endoscope system or a microscope system.

11. A control method executed by a computer, the control method comprising:

emitting at least two light beams having peak wavelengths different from each other;

generating a multiplexed light beam by using the at least two light beams;

detecting the multiplexed light beam emitted by the light source with a color sensor;

producing a plurality of outputs from the color sensor including a first output and a second output based on the multiplexed light beam and calculating a wavelength shift amount of the multiplexed light beam on a basis of a ratio of the first output and the second output produced by the color sensor.

12. A light source system comprising:

a light source configured to emit a light beam;

a color sensor configured to detect the light beam emitted by the light source and produce a plurality of outputs including a first output and a second output based on the light beam; and circuitry configured to perform calculation of a wavelength shift amount of the light beam on a basis of a ratio of the first output and the second output produced by the color sensor and on a basis of the first output having a highest value among the plurality of outputs from the color sensor.

* * * * *